United States Patent [19]

Lupo et al.

[11] Patent Number: 5,116,925
[45] Date of Patent: May 26, 1992

[54] AMPHIPHILIC MONOMERS AND POLYMERS AND FILM COMPRISING AT LEAST ONE UNIMOLECULAR LAYER THEREOF

[75] Inventors: Donald Lupo, Eppstein/Taunus; Werner Prass, Mainz; Ude Scheunemann, Liederbach, all of Fed. Rep. of Germany

[73] Assignee: Hoechst Aktiengesellschaft, Frankfurt am Main, Fed. Rep. of Germany

[21] Appl. No.: 595,543

[22] Filed: Oct. 11, 1990

Related U.S. Application Data

[62] Division of Ser. No. 508,007, Apr. 10, 1990, abandoned.

Foreign Application Priority Data

Apr. 12, 1989 [DE] Fed. Rep. of Germany ....... 3911929

[51] Int. Cl.$^5$ .................. C08F 22/10; C08F 22/36
[52] U.S. Cl. .................. 526/323.1; 526/303.1; 526/304; 526/306; 526/307.5; 526/310
[58] Field of Search ............... 526/307.5, 323.1, 304, 526/310

[56] References Cited

U.S. PATENT DOCUMENTS 4,728,696  3/1988  Van Phung et al. ............... 526/304

FOREIGN PATENT DOCUMENTS 8303165  9/1983  World Int. Prop. O.

OTHER PUBLICATIONS

Saykh-Zade, S. I. et al., Synthesis of Aliphatic Mixed Diethylene Glycol Esters of Acrylic and Methacrylic Acids, Zh. Khim. 1976, Abstract No. 18 Zh 137. Ibid. CA 86 (1):54960g.

*Primary Examiner*—Joseph L. Schofer
*Assistant Examiner*—Fred Zitomer
*Attorney, Agent, or Firm*—Curtis, Morris & Safford

[57] ABSTRACT

Amphiphilic monomers having mixed-chain structures of the general formulae (I) or (II)

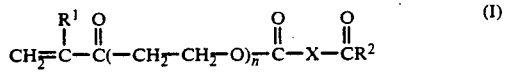

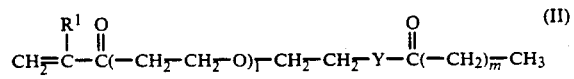

where
Y is —O— or —NH—,
X is a group of the formula —(CH$_2$)$_n$— or —(CH$_2$—O—CH$_2$)$_n$—,
l is an integer from 0 to 10,
m is an integer from 10 to 26,
n is an integer from 1 to 10,
R$^1$ is hydrogen, methyl, chlorine, cyano, fluorine or bromine, and
R$^2$ is O-alkyl or NH-alkyl, are polymerized alone or together with other comonomers. The polymers obtained are suitable for preparing ultra-thin films on a suitable base material.

10 Claims, No Drawings

AMPHIPHILIC MONOMERS AND POLYMERS AND FILM COMPRISING AT LEAST ONE UNIMOLECULAR LAYER THEREOF

This application is a division of application Ser. No. 508,007, filed Apr. 10, 1990, now abandoned.

DESCRIPTION

The present invention relates to specific amphiphilic monomers having long alkyl chains, to polymers thereof, to a film formed from at least one unimolecular layer of these molecules on a solid base material (=so-called layer elements), and to processes for preparing the monomers, the polymers and the layer elements.

Ordered layers of organic polymers having long-chain side groups are predominantly prepared using the Langmuir-Blodgett (LB) technique whereby molecules are spread out on a water surface and compressed to arrange the long alkyl side groups in a parallel arrangement. While a constant surface pressure is applied, the molecules are applied to a substrate by dipping, one unimolecular layer per dipping operation being transferred with its order in tact.

LB films are constructed using amphiphilic molecules, i.e. molecules which have a hydrophilic end ("head") and a hydrophobic end ("tail"). It has already been sought to make more stable LB films by preparing polymeric LB films.

One previous attempt consisted in polymerizing unsaturated amphiphilics after the preparation of the film. However, films have also been prepared directly using organic polymers having long alkyl side chains (International Patent Application WO83/03165 and R. Elbert, A. Laschewsky and H. Ringsdorf, J. Am. Chem. Soc. 107, 4134–4141 (1985)). But both kinds of polymeric film have more defects than monomeric films.

If the polymerization takes place in the layer, the layer contracts in virtually all cases, giving rise to defects. In the case of films from copolymers which contain a hydrophobic comonomer having two long-chain alkyl groups as copolymerized units, as described by A. Laschewsky, H. Ringsdorf, G. Schmidt and J. Schneider in J. Am. Chem. Soc. 109, 788–796 (1987), the randomly incorporated hydrophilic comonomers can give rise to hydrophilic loops of different sizes which lead to irregularities in the layer thickness.

Uniform LB layers of homopolymers can in general only be constructed if the alkyl side chain and the polymer main chain are separated by a flexible hydrophilic segment, a hydrophilic spacer. However, the monomers described by R. Elbert, A. Laschewsky and H. Ringsdorf in J. Am. Chem. Soc. 107, 4134–4141 (1985), which are two-chain amphiphilics, can only be prepared at great expense. In the case of homopolymers having two long-chain alkyl groups per monomer unit we have found that, owing to the large amount of space occupied by the two alkyl groups, the hydrophilic spacers do not bring about complete decoupling.

DE-A-3,843,194 already proposes films from polymers which are preparable from mixed-chain, amphiphilic monomers available in multistage syntheses.

It is an object of the present invention to prepare further, synthetically simpler monomers whose homopolymers permit good decoupling of the ordering tendency of alkyl side chains and polymer main chains, are particularly easily transferable to base materials, and form a firmer film.

This object is achieved in the present invention by the synthesis of single-chain amphiphilic monomers whose a polar moiety is incorporated in a simple manner with long-chain alcohols or amines. The single-chain amphiphilics make it possible to use relatively short hydrophilic spacers, which are simpler to synthesize, for realizing the decoupling of the ordering tendency of the polymer main chain (tendency to form polymer coils) and of the alkyl side chain (tendency to crystallize) even in the homopolymers. The monomer units have the following general structure (formula I or formula II):

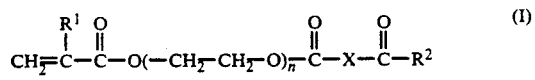

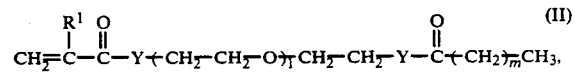

where

X is $(CH_2)_n$ or $(CH_2-O-CH_2)_n$,

Y is O or NH, l is an integer from 0 to 10, m is an integer from 10 to 26, preferably from 13 to 21, n is an integer from 1 to 10, $R^1$ is H, $CH_3$, Cl, CN, F or Br, and $R^2$ is an O-alkyl radical or NH-alkyl radical having an alkyl chain of at least 8 carbon atoms, preferably n-alkyl of 12–22 carbon atoms.

The monomers of the general formula (I) can be prepared, first of all, by reacting a dicarboxylic acid of the general formula (III)

$$HOOC-X-COOH \qquad (III)$$

or an activated derivative thereof, for example an anhydride, ester or halide, with an unsaturated alcohol of the general formula (IV)

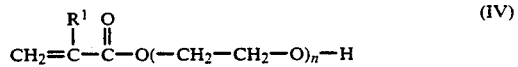

to give the monoester and subsequent condensation with a long-chain alcohol or primary amine of the general formula $R^2H$.

On the other hand, they can also be prepared by the reverse sequence, i.e. by reacting the dicarboxylic acid of the formula (III) or a reactive derivative thereof with a long-chain alcohol or primary amine $R^2H$ followed by esterification of the intermediate with the unsaturated alcohol of the formula (IV).

The monomers of the general formula (II) are synthesized by reacting a carboxylic acid (V)

or a reactive derivative thereof with an alcohol or primary amine of the general formula (VI)

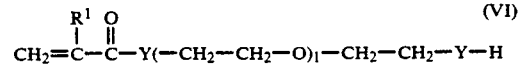

preferably in the presence of a tertiary amine. Examples of reactive carboxylic acid derivatives which can be used are carbonyl chloride and carboxylic anhydride.

To prepare the polymers according to the present invention, these monomers are homopolymerized or else copolymerized with one or more other monomers. The comonomers can likewise be unsaturated monomers having long alkyl chains of at least 8 carbon atoms, for example compounds of the general formula (VII)

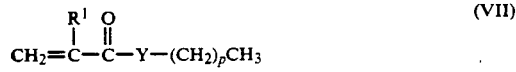

(VII)

where p is an integer from 7 to 21, or other monomers of the formula (I) or (II) or monomers as described in the abovementioned publications and DE-A-38 431 904. These references are therefore expressly incorporated herein.

But the comonomers used can also be vinyl monomers which contain a hydrophilic group and preferably are water-soluble, e.g. itaconic acid, fumaric acid, maleic acid, acrylic, cyanoacrylic or methacrylic acid or derivatives thereof. The copolymers according to the present invention are prepared starting from at least 10% by weight, preferably at least 20% by weight, of a monomer of the general formula (I) or (II). The polymerization is preferably carried out as a free radical polymerization, in particular in the presence of a free radical former. The free radical formers used are for example azobisisobutyronitrile and peroxides. By adding regulators (for example mercaptans such as octadecanethiol) it is possible to obtain polymers having a smaller molecular weight. The polymers according to the present invention are highly suitable for preparing a layer element from as low a molecular weight as about 5000 daltons upward.

To prepare the films according to the present invention, the organic polymers or mixtures which contain the polymers according to the present invention, preferably in an amount of 10–100% by weight, are dissolved in an essentially volatile water-immiscible solvent and spread out on the surface of an aqueous solution in a film balance. The dimensions of the surface area, the spread-out volume and the concentration of the solution make it possible to calculate the average area per repeat unit. Phase transitions on compressing the molecules can be monitored by plotting the force-area isotherm.

The molecules are compressed with a barrier and the alkyl chains become oriented essentially perpendicularly to the interface as the surface pressure increases.

During the process of compression the molecules become automatically organized at the interface into a highly ordered unimolecular film whose constant thickness is determined essentially by the chain length of the alkyl side chains of the polymers and their tilt angle (i.e. the angle by which the molecular chains on the water surface tilt away from the normal). The typical thickness of such a film is 2–3 nm.

The film is transferable with its order in tact from the water surface to a suitable base material by immersing or withdrawing said base material under constant surface pressure.

The subphase used for monofilm preparation is usually water or an aqueous solution. However, it is also possible to use other liquids of high surface tension, for example glycerol, glycol, dimethyl sulfoxide, dimethylformamide or acetonitrile.

Suitable base materials are all solid, preferably dimensionally stable substrates. The substrates which are used as base materials can for example transparent or opaque, electrically conducting or insulating. The substrate can be hydrophobic or hydrophilic. The surface of a basically hydrophilic substrate to which the LB layer is applied can have been hydrophobized. The surface of the substrate to be coated should be as clean as possible so as not to interfere with the formation of a thin, ordered layer. In particular the presence of surface-active substances on the surface of the substrate to be coated can impair the formation of a layer. It is possible that before the LB film is applied the surface of the substrate to be coated be initially provided with an interlayer in order to improve for example the adhesion of the film to the substrate.

Materials used for the substrate can be for example metals, such as gold, platinum, nickel, palladium, aluminum, chromium, niobium, tantalum, titanium, steel and the like. Other suitable materials for substrates are plastics, for example polyesters, e.g. polyethyleneterephthalate or polybutyleneterephthalate, polyvinyl chloride, polyvinylidene chloride, polytetrafluoroethylene, polystyrene, polyethylene and polypropylene.

It is also possible to use semiconductors, such as silicon, germanium or gallium arsenide, or else glass, silicon dioxide, ceramic materials or cellulose products as substrate materials. The surface of glass and other hydrophilic substrates can if necessary be hydrophobized in a conventional manner by reaction with alkylsilanes or hexamethyldisilazane. Which substrate material is chosen depends primarily on the purpose of the layer elements prepared from the film according to the present invention. Optical elements are in general made with transparent substrates. If the layer elements according to the present invention are used for example in electronics or in electrochemical processes, the substrates used are in particular electroconductive materials, such as metals or indium tin oxide, or metallic surface layers, for example on plastics sheeting or glass.

The substrates used as base materials for the films according to the present invention may have any desired shape, depending on the intended use. They can be for example filmlike, sheetlike, platterlike, tapelike or else cylindrical or have any other desired shape. In general, the base materials will be flat, planar substrates, such as films, sheets, platters, tapes and the like. The surface of the substrate to be coated is preferably smooth, as is customary for the production of LB films. In the case of flat, planar substrates the films according to the present invention can be applied to either or both of the surfaces of the substrate.

The polymers according to the present invention are notable for easy preparability of a multilayer structure having few defective areas but having a good heat stability.

Such substrate-supported films are suitable for example for optical waveguide systems or for fabricating filters for optical purposes. Owing to the low critical surface tension, the films are also suitable for improving the frictional properties of materials for producing protective cover layers and for further relevant applications.

The invention is further illustrated by the following Examples:

EXAMPLE 1

Synthesis of monomer 4

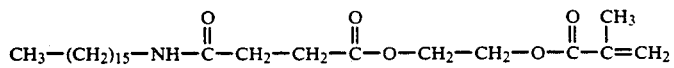

6.0 g (60 mmol) of succinic anhydride and 4.7 g (60 mmol) of pyridine are dissolved in 200 ml of dry toluene and admixed at 25° C. with stirring in the absence of moisture with a solution of 6.5 g (50 mmol) of 2-hydroxyethyl methacrylate and 5 mg of 2,6-di-tert-butyl-p-cresol in 50 ml of dry toluene, added in the course of 5 minutes. After the addition has ended, the reaction mixture is heated and stirred at 70°–80° C. for 16 hours. After cooling down, the solvent is removed in vacuo and the liquid obtained is dried under an oil pump vacuum.

9.26 g (80.5%) are obtained of a clear liquid. $^1$H NMR (100 MHz, CDCl$_3$): $\delta = 1.9$ (t, 3H; —CH$_3$), 2.65 (s, 4H; —CO—CH$_2$—CH—CO—), 4.35 (s, 4H; —O—CH$_2$—CH$_2$—O—), 5.6, 6.1 (AB, 2H; =CH$_2$).

To a solution of 9.66 g of hexadecylamine and 12.0 g (55 mmol) of the above-prepared succinic ester in 250 ml of dry methylene chloride is added at 0° C. with stirring in the absence of moisture a solution of 10.32 g (50 mmol) of dicyclohexylcarbodiimide and 150 mg of freshly recrystallized N,N-dimethylaminopyridine in 100 ml of dry methylene chloride in the course of 20 minutes. The mixture is stirred at 0° C. for 6 hours, the resulting precipitate is filtered off, and the solvent is removed in vacuo. The crude product is purified by column chromatography (silica gel Si60, eluent: 1:1 hexane/ethyl acetate).

13.8 g (30.4 mmol, 76%) are obtained of a white powder which melts at 48° C.

$^1$H NMR (100 MHz, CDCl$_3$): d = 0.9 (t, 3H; —CH$_3$ alkyl chain), 1.1–1.5 (m, 28H; —CH$_2$—alkyl chain), 1.9 (t, 3H; —CH$_3$ methacrylic acid), 2.3–2.8 (m, 4H; —CO—CH$_2$—CH$_2$—CO—), 3.1–3.3 (m, 2H; —CH$_2$—N) 4.35 (s, 4H; —O—CH$_2$—CH$_2$—O—), 5.6, 6.1 (AB, 2H; =CH$_2$).

EXAMPLE 2

Synthesis of monomer 7

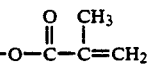

13.0 g (0.1 mol) of 2-hydroxyethyl methacrylate, 13.4 g of diglycolic acid and 10 mg of 2,6-di-tert-butyl-p-cresol, dissolved in 250 ml of dry tetrahydrofuran, are introduced at 0° C. in the absence of moisture and admixed by stirring with a solution of 20.6 g (0.1 mol) of dicyclohexylcarbodiimide and 250 mg of freshly recrystallized N,N-dimethylaminopyridine in 50 ml of dry THF added over 10 minutes. The mixture is subsequently stirred at 0° C. for two hours and then warmed to room temperature with stirring. The next day the resulting precipitate is filtered off and the solvent is removed in vacuo. The crude product thus obtained is purified by column chromatography (silica gel Si60, eluent 100:15:1 chloroform/methanol/glacial acetic acid). 18 g (73 mmol, 73%) are obtained of pure product.

$^1$H NMR (100 MHz, CDCl$_3$): $\delta = 1.9$ (m, 3H; —CH$_3$), 4.25 (s, 4H; —CO—CH$_2$—O—CH$_2$—CO—), 4.3–4.5 (m, 4H; —O—CH$_2$—CH$_2$—O—), 5.6, 6.1 (AB, 2H; =CH$_2$).

To a solution of 13.5 g (50 mmol) of octadecanol and 13.5 g (50 mmol) of the above-prepared diglycolic monoester in 250 ml of dry methylene chloride is added at 0° C. with stirring in the absence of moisture a solution of 10.3 g (50 mmol) of dicyclohexylcarbodiimide and 150 mg of freshly recrystallized N,N-dimethylaminopyridine in 100 ml of dry methylene chloride added over 20 minutes. The mixture is subsequently stirred at 0° C. for two hours, the resulting precipitate is filtered off, the organic phase washed with water and dried with sodium sulfate, and the solvent is removed in vacuo. Uncoverted octadecanol is recovered by recrystallization from hexane. The product thus prepurified is purified by column chromatography (silica gel Si60, eluent: 8:1 hexane/ethyl acetate). The second fraction contains 4.5 g (9.0 mmol, 10%) of a white waxy material which melts at between 36.5° and 37.5° C.

$^1$H NMR (100 MHz, CDCl$_3$): $\delta = 0.9$ (t, 3H; —CH$_3$ alkyl chain), 1.1–1.8 (m, 32H, —CH$_2$ alkyl chain), 1.9 (m, 3H; —CH$_3$ methacrylic acid), 4.0–4.5 (m, 10H; —CO—CH$_2$—O—CH$_2$—CO—, —CH$_2$—O—CO—, —O—CH$_2$—CH$_2$—O—), 5.6, 6.1 (AB, 2H; =CH$_2$).

EXAMPLE 3

Synthesis of monomer 3

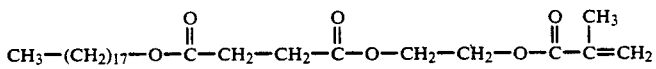

13.3 g (50 mmol) of octadecanol and 6.1 g (60 mmol) of triethylamine are dissolved in 100 ml of dry toluene and admixed at 20° C. with stirring in the absence of moisture with a solution of 9.0 g (90 mmol) of succinic anhydride in 200 ml of dry toluene added over 15 minutes. After the addition has ended, the reaction mixture is heated and refluxed for 40 hours. After cooling down, the reaction solution is extracted with 300 ml of 1 M HCL, the organic phase is dried with MgSO$_4$, and the solvent is removed in vacuo. To purify the crude product it is subsequently recrystallized once from hexane and once from methanol. 10.70 g (85%) are obtained of a white powder which melts at between 83° and 85° C.

$^1$ NMR (100 MHz, CDCl$_3$): $\delta = 0.9$ (t, 3H; —CH$_3$), 1.0–1.8 (m, 32H; —CH$_2$—alkyl chain), 2.65 (m, 4H; —CO—CH$_2$—CH$_2$—CO—), 4.05 (t, 2H; —CH$_2$—O—).

To a solution of 5.49 g (42.4 mmol) of 2-hydroxyethyl methacrylate, 50 mg of 2,5-di-t-butyl-p-cresol and 10.0 g (27 mmol) of the above-prepared succinic ester in 300 ml of dry methylene chloride is added at 0° C. by stirring in the absence of moisture a solution of 6.1 g (29.5 mmol) of dicyclohexylcarbodiimide and 130 mg of freshly recrystallized N,N-dimethylaminpryridine in 100 ml of dry methylene chloride added over 20 minutes. The mixture is stirred at 0° C. for 1 hour and then warmed to room temperature. The next day the precipitate formed is filtered off, the solution is washed with water and dried with $Na_2SO_4$, and the solvent is removed in vacuo. The crude product is purified by recrystallization from ethanol. 8.59 g (17.8 mmol, 66%) are obtained of a white powder which melts at 36°–37° C.

$^1$H NMR (100 MHz, $CDCl_3$): $\delta$=0.9 (t, 3H; —$CH_3$ alkyl chain, 1.1–1.8 (m, 32H, —$CH_2$—alkyl chain), 1.9 (t, 3H; —$CH_3$ methacrylic acid), 2.5–2.8 (m, 4H; —CO—$CH_2$—$CH_2$—CO—), 4.05 (t, 2H; —$CH_2$—O—CO—) 4.35 (s, 4H; —O—$CH_2$—$CH_2$—O—), 5.6, 6.1 (AB, 2H; =$CH_2$ methacrylic acid).

EXAMPLE 4

Synthesis of monomer 11

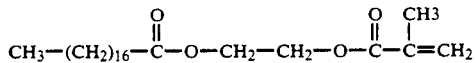

To a solution of 10 g (33 mmol) of stearyl chloride in 100 ml of dry methylene chloride is added over 20 minutes at 5° C. in the absence of moisture a solution of 4.01 ml (4.3 g, 33 mmol) of 2-hydroxyethyl methacrylate, 5.55 ml (4.05 g, 40 mmol) of triethylamine and 20 mg of 2,6-di-tert-butyl-p-cresol in 50 ml of dry methylene chloride. After the addition has ended, the mixture is subsequently stirred at 5° C. for 30 minutes; it is then warmed to 20° C. and subsequently stirred for a further two hours. The next day the reaction mixture is extracted twice with 1 MHCl, the organic phase is dried with sodium sulfate and the solvent is removed in vacuo. The crude product is purified by recrystallizing it twice from 50 ml of methanol and hexane each time.

8.6 g (22 mmol, 66%) are obtained of a waxy white material.

$^1$H NMR (100 MHz, $CDCl_2$): $\delta$=0.9 (t, 3H; —$CH_3$ alkyl chain), 1.5–1.8 (m, 30H; —$CH_2$—alkyl chain), 1.9–2.0 (m, 3H; —$CH_3$ methacrylic acid), 2.2–2.5 (m, 2H; —$CH_2$—CO—), 4.3 (s, 4H; —O—$CH_2$—$CH_2$—O—), 5.6, 6.1 (AB, 2H; =$CH_2$).

EXAMPLE 5

Free radical homopolymerization of monomer 4

1 g of the monomer prepared in Example 1 is dissolved in 20 ml of tetrahydrofuran and admixed with 7.0 mg of azobisisobutyronitrile. The solution is introduced into a three-neck flask equipped with a reflux condenser (with gas discharge tube and bubble counter), a thermometer and a gas inlet tube and purged with nitrogen at room temperature for one hour. The solution is then brought to reflux point (internal temperature: 65° C.) and refluxed for 7 hours. All the time the reaction mixture is continuously stirred with a magnetic stirrer and purged with nitrogen. The polymer is precipitated by pouring the reaction solution into methanol, and filtered off with suction. 710 mg are obtained of a white finely granular material which is insoluble in hexane and methanol and soluble in tetrahydrofuran. A molecular weight determination by gel permeation chromatography produced an Mw of 26,000 and an Mn of 17,000 daltons (polystyrene calibration).

EXAMPLE 6

Free radical homopolymerization of monomer 7

1 g of the monomer prepared in Example 2 is dissolved in 10 ml of tetrahydrofuran and admixed with 6.8 mg of azobisisobutyronitrile. The solution is introduced into a three-neck flask equipped with a reflux condenser (with gas discharge tube and bubble counter), a thermometer and a gas inlet tube and purged with nitrogen at room temperature for one hour. The solution is then brought to reflux point (internal temperature: 65° C.) and refluxed for 6 hours. All the time the reaction mixture is continuously stirred with a magnetic stirrer and purged with nitrogen. The polymer is precipitated by pouring the reaction solution into methanol, and filtered off with suction. 590 mg are obtained of a white finely granular material which is insoluble in hexane and methanol and soluble in tetrahydrofuran. A molecular weight determination by gel permeation chromatography produced an Mw of 26,000 and an Mn of 18,000 daltons (polystyrene calibration).

EXAMPLE 7

Free radical copolymerization of monomer 11 with 2-hydroxyethyl methacrylate 2 g (5.04 mmol) of 2-hydroxyethyl methacrylate are dissolved in 20 ml of tetrahydrofuran and admixed with 8.3 mg of azobisisobutyronitrile. The solution is introduced into a three-neck flask equipped with a reflux condenser (with gas discharge tube and bubble counter), a thermometer and a gas inlet tube and purged with nitrogen at room temperature for one hour. The solution is then brought to reflux point (internal temperature: 65° C.) and refluxed for 6 hours. All the time the reaction mixture is continuously stirred with a magnetic stirrer and purged with nitrogen. The polymer is precipitated by pouring the reaction solution into methanol, and filtered off with suction. To free the product of residual monomer it is then twice dissolved in tetrahydrofuran and precipitated by pouring into methanol. 1.4 g are obtained of a white finely granular material which is insoluble in hexane and methanol and soluble in tetrahydrofuran. A molecular weight determination by gel permeation chromatography produces an Mw of 51,000 and an Mn of 27,000 daltons (polystyrene calibration). An elemental analysis indicating 66.9% of C and 10.2% of H suggests that the copolymer is composed of 1 part of monomer with a long-chain substituent and 1.4 parts of 2-hydroxyethyl methacrylate.

EXAMPLE 8

Film production by the Langmuir-Blodgett method

A microscope slide made of glass (76 mm × 26 mm) is cleaned by the following method:

The slide is placed for an hour in a hot, freshly prepared mixture at 60° C. of four parts of concentrated $H_2SO_4$ and one part of 30% strength $H_2O_2$, rinsed off with clean water and sonicated in a cleaning solution (Extran/AP 11, concentration 2–4 g/l) at 50° C. for 15 minutes. It is then again rinsed off thoroughly with clean water and dried in a warm air stream. It is then hydrophobized by treating it with hexamethyldisilazane vapor (10 minutes at 70° C.). Multilayers of the polymer prepared in Example 5 are transferred by the Langmuir-Blodgett technique to the glass slide by spreading 250 cm³ of a solution of 5.1 mg of the polymer in 10 cm³ of 9:1 (v/v) methylene chloride/tetrahydrofuran on an aqueous subphase at a subphase temperature of 20° C. in a Langmuir film balance. By reducing the monolayer-covered part of the water surface the surface pressure is adjusted to 15 mN/m and kept constant at that value. The slide is then dipped vertically downward through the water surface into the film balance at a speed of 20 mm/min and, following a brief pause of 10 seconds at the lower reversal point, removed again at a speed of 10 mm/min. A monolayer transfers to the slide not only during the process of immersion but also during the process of withdrawal. A total of 10 double layers are transferred to the slide by repeating the dipping process with a one minute delay time at the upper reversal point after each dip. The transfer rate is 95%. Optically clear, transparent films are obtained even if 50 or more monolayers are transferred.

The same technique is also used to obtain films from the polymers prepared in Examples 6 and 7 under the following transfer conditions:

| Polymer of Example: | 6 | 7 |
|---|---|---|
| Subphase temperature: | 30° C. | 30° C. |
| Surface pressure: | 30 mN/m | 25 mN/m |
| Transfer rate: | 80% | 90% |

EXAMPLE 9

Ellipsometric film thickness and refractive index measurements

A silicon platelet (40 mm × 10 mm) is cut out of a silicon wafer and cleaned as follows:
1. Treatment for 1 hour in a hot (60° C.), freshly prepared mixture of one part of 30% strength $H_2O_2$ and four parts of concentrated $H_2SO_4$. This is followed by a rinse with clean water.
2. Immersion for 30 seconds in $NH_4F$ buffered HF solution followed again by rinsing with clean water. Following this treatment the silicon platelets are hydrophobic (contact angle with water: 75°).

Layers of the polymers prepared in Examples 5, 6 and 7 are transferred by the Langmuir-Blodgett technique to the silicon platelet under the same conditions as in Example 8. Samples are prepared with 10, 30, 50 and 70 monolayers of the individual polymers, and the thicknesses and refractive indices of the LB films are measured ellipsometrically.

| Results of measurements: | | | |
|---|---|---|---|
| Polymer of Example: | 5 | 6 | 7 |
| Refractive index at 633 nm: | 1.51 | 1.488 | 1.499 |
| Film thickness in nm/monolayer: | 1.42 | 1.92 | 2.2 |

EXAMPLE 10

Measurements of Thermal Stability

Silicon platelets (40 mm × 10 mm) are cut out of a thermally oxidized silicon wafer (thickness of oxide layer:

160 nm) and placed for one hour at 60° C. in a freshly prepared mixture of one part of 30% strength $H_2O_2$ and four parts of concentrated $H_2SO_4$. Following a thorough rinse with clean water the platelet is sonicated in an alkaline cleaning bath (Extran/AP 11, concentration 2–4 g/l) at 50° C. for 15 minutes, thoroughly rinsed off with clean water and dried in a warm air stream. It is then hydrophobized with hexamethyldisilazane vapor (10 minutes at 70° C.)

It is coated with 8 monolayers each of the polymers prepared in Examples 5, 6 and 7 by the LB technique as described in Example 8.

The coated platelet is heated up in a specific apparatus in accordance with a linear temperature gradient (0.5° C./sec). During the heating-up, the thickness of the LB film is measured by measuring the intensity of a perpendicularly polarized laser beam (633 nm) reflected by the sample. The temperature at which the first change in the film thickness occurs is 195° C. in the case of films of the polymer prepared in Example 5, 85° C. in the case of films of the polymer prepared in Example 6 and again 195° C. in the case of films of the polymer prepared in Example 7. (For comparison: in the case of LB films of 22-tricosenoic acid this temperature is 70° C.).

EXAMPLE 11

Measurements of the critical surface tension

Silicon platelets (40 mm × 10 mm) are cleaned as in Example 9 and are coated with eight monolayers each of the polymers prepared in Examples 5, 6, and 7 as described in Example 8.

Droplets of a number of liquid n-alkanes ($C_9H_{20}$—$C_{16}H_{34}$) are applied to the surfaces of the transferred layers, and the contact angles of the droplets with the surface are measured. These contact angles are used to determine the critical surface tension by the method of Zisman. The following values are obtained:

| Polymer of Example | Critical surface tension in mN/m |
|---|---|
| 5 | 25.1 |
| 6 | 22.8 |
| 7 | 25.2 |

(For comparison: in the case of a polyethylene surface this measurement produces a value of 31 mN/m).

EXAMPLE 12

The table which follows shows additional monomers prepared by methods similar to the syntheses of Examples 1 to 4.

Table of synthesized monomers:

| Compound No. | Structural formula |
|---|---|
| 1 | $CH_3-(CH_2)_{13}-O-\underset{\underset{O}{\|}}{C}-CH_2-CH_2-\underset{\underset{O}{\|}}{C}-O-CH_2-CH_2-O-\underset{\underset{O}{\|}}{C}-\underset{\underset{CH_3}{\|}}{C}=CH_2$ |

-continued

Table of synthesized monomers:

| Compound No. | Structural formula |
|---|---|
| 2 | $CH_3-(CH_2)_{15}-O-\overset{O}{\overset{\|}{C}}-CH_2-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 3 | $CH_3-(CH_2)_{17}-O-\overset{O}{\overset{\|}{C}}-CH_2-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 4 | $CH_3-(CH_2)_{15}-NH-\overset{O}{\overset{\|}{C}}-CH_2-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 5 | $CH_3-(CH_2)_{17}-NH-\overset{O}{\overset{\|}{C}}-CH_2-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 6 | $CH_3-(CH_2)_{15}-O-\overset{O}{\overset{\|}{C}}-CH_2-O-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 7 | $CH_3-(CH_2)_{17}-O-\overset{O}{\overset{\|}{C}}-CH_2-O-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 8 | $CH_3-(CH_2)_{15}-NH-\overset{O}{\overset{\|}{C}}-CH_2-O-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 9 | $CH_3-(CH_2)_{17}-NH-\overset{O}{\overset{\|}{C}}-CH_2-O-CH_2-\overset{O}{\overset{\|}{C}}-O-CH_2-CH_2-O-\overset{O}{\overset{\|}{C}}-\overset{CH_3}{\overset{\|}{C}}=CH_2$ |
| 10 | $CH_3-(CH_2)_{16}-\overset{O}{\overset{\|}{C}}-NH-(CH_2-CH_2-O-)_3-CH_2-CH_2-NH-\overset{O}{\overset{\|}{C}}-\overset{CH_3}{\overset{\|}{C}}=CH_2$ |
| 11 | $CH_3-(CH_2)_{16}-\overset{O}{\overset{\|}{C}}-O-CH_2-CH_2-O-\overset{O}{\overset{\|}{C}}-\overset{CH_3}{\overset{\|}{C}}=CH2$ |

What is claimed is:

1. A layer element comprising a film of at least one unimolecular layer of an amphiphilic compound on a solid base material, wherein the layer contains a polymer obtained by polymerization of a monomer of the general formula (I) or (II)

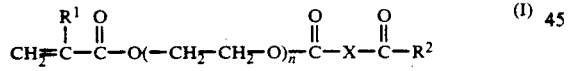  (I)

  (II)

where
X is $(CH_2)_n$ or $(CH_2-O-CH_2)_n$,
Y is O or NH,
l is an integer from 0 to 10, m is an integer from 10 to 26, n is an integer from 1 to 10,
$R^1$ is H, $CH_3$, Cl, CN, F or Br, and $R^2$ is an O-alkyl radical or NH-alkyl radical having an alkyl chain of at least 8 carbon atoms.

2. A layer element comprising a film of at least one unimolecular layer of an amphiphilic compound on a solid base material, wherein the layer contains a copolymer obtained by copolymerization of at least 20% by weight of one or more monomers of the formula (I) and/or (II) of claim 1 with or without further hydrophilic comonomers.

3. A process for preparing a layer element as claimed in claim 1, which comprises dissolving the polymer in a volatile organic water-immiscible solvent, spreading the solution on a water/air interface, evaporating the solvent, compressing the resulting layer, and transferring the layer to a solid base material.

4. A process for preparing a layer element as claimed in claim 2, which comprises dissolving the copolymer in a volatile organic water immiscible solvent, spreading the solution on water/air interface, evaporating the solvent, compressing the resulting layer, and transferring the layer to a solid base material.

5. A layer element as claimed in claim 1, wherein $R^2$ is an O-alkyl radical or NH-alkyl radical having an alkyl chain of 12-22 carbon atoms.

6. A layer element comprising a film of at least one unimolecular layer of an amphiphilic compound on a solid base material, wherein the layer contains a polymer obtained by polymerization of a monomer of the general formula (I) or (II)

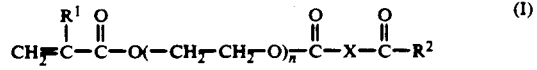  (I)

  (II)

where
X is $(CH_2)_n$ or $(CH_2-O-CH_2)_n$,
Y is O or NH, l is an integer from 0 to 10, m is an integer from 13 to 21, n is an integer from 1 to 10, $R^1$ is H, $CH_3$, Cl, CN, F or Br, and $R^2$ is an O-alkyl radical or NH-alkyl radical having an alkyl chain of at least 8 carbon atoms.

7. A layer element comprising a film of at least one unimolecular layer of an amphiphilic compound on a solid base material, wherein the layer contains a copolymer obtained by copolymerization of at least 20% by weight of one or more monomers of the formula (I) and/or (II) of claim 6 with or without further hydrophilic comonomers.

8. A process for preparing a layer element as claimed in claim 6, which comprises dissolving the polymer in a volatile organic water-immiscible solvent, spreading the solution on a water/air interface, evaporating the solvent, compressing the resulting layer, and transferring the layer to a solid base material.

9. A process for preparing a layer element as claimed in claim 7, which comprises dissolving the copolymer in a volatile organic water-immiscible solvent, spreading the solution on a water/air interface, evaporating the solvent, compressing the resulting layer, and transferring the layer to a solid base material.

10. A layer element as claimed in claim 6, wherein $R^2$ is an O-alkyl radical or NH-alkyl radical having an alkyl chain of 12-22 carbon atoms.

* * * * *